United States Patent [19]

Loge

[11] 4,217,101
[45] Aug. 12, 1980

[54] DENTAL HANDPIECE

[75] Inventor: Hans Logé, Biberach an der Riss, Fed. Rep. of Germany

[73] Assignee: Kaltenbach & Voight GmbH & Co., Biberach an der Riss, Fed. Rep. of Germany

[21] Appl. No.: 935,799

[22] Filed: Aug. 22, 1978

[30] Foreign Application Priority Data

Sep. 20, 1977 [DE] Fed. Rep. of Germany ... 7729110[U]

[51] Int. Cl.$^2$ ................................................ A61C 1/08
[52] U.S. Cl. ....................................... 433/126; 433/82
[58] Field of Search ...................... 285/136; 32/26, 27; 433/126, 82

[56] References Cited

U.S. PATENT DOCUMENTS

| | | | |
|---|---|---|---|
| 3,894,338 | 7/1975 | Loge et al. | 32/27 |
| 4,106,796 | 8/1978 | Asztalos et al. | 285/136 |

Primary Examiner—Robert Peshock
Attorney, Agent, or Firm—Scully, Scott, Murphy & Presser

[57] ABSTRACT

A dental handpiece having a holding sleeve, an air-driven unit mounted at one end of the sleeve to drive a dental tool, and a connecting member releasably and relatively rotatably connected to the other end of the sleeve. A supply hose for conveying fluid pressure media is coupled releasably and non-rotatably to the end of the connecting member remote from the sleeve, and communicating fluid pressure lines in the connecting member and in the sleeve convey fluid pressure media between the hose and consumers of fluid pressure media at the free end of the sleeve, such as the tool-drive unit. The releasable connection between the connecting member and the sleeve is provided by a pin on the connecting member which is received by a passage in the sleeve. The fluid pressure lines in the connecting member extend also generally lengthwise along the pin, but terminate in radial portions having outlet apertures which are axially spaced along the outer periphery of the pin. Each outlet aperture is located between a respective pair of seals engaging between the wall of the passage and the outer periphery of the pin, and communication with a corresponding fluid pressure line in the sleeve is established, when the pin is inserted into a releasable detent position in the passage, via an annular duct formed in the wall of the passage.

14 Claims, 4 Drawing Figures

DENTAL HANDPIECE

This invention relates to a dental handpiece comprising a holding sleeve by which the handpiece may be manually manipulated, a tool-drive unit mounted at one end of said sleeve and adapted for operation by a fluid pressure medium, a connecting member releasably connected to said sleeve at the opposite end thereof, said connecting member and said sleeve being relatively rotatable and said connecting member being adapted to be coupled releaseably and non-rotatably with a fluid pressure supply hose, and communicating fluid pressure lines provided in said holding sleeve and in said connecting member for conveying fluid pressure media between said supply hose and consumers of fluid pressure media such as the tool-drive unit.

The fluid pressure media conveyed through the supply hose to the handpiece will generally be pressure air for operating the drive unit, (for example an air motor or an air turbine), the unit having a hollow rotor shaft in which a dental treatment implement, for example a drill, is inserted, and also cooling air and cooling water for cooling the zone of the tooth-treatment implement, optionally whilst forming a spray, and exhaust air conveyed-back from the driving unit. The freely rotatable arrangement of the sleeve relative to the connecting member and therewith relative to the supply hose facilitates for the dentist utilisation of the handpiece during dental treatment, whereas the releasable connection of the sleeve and connecting member is based on the fact that the sleeve must be relatively frequently separated from the connecting member and therewith from the supply hose, in order to clean the drive unit disposed in the sleeve and to oil it and sterilise it, or to replace the sleeve by another model having other dimensions and capacity data of the driving unit.

A dental handpiece of the above type is known from German Utility Model 72 47 029, in which the connecting member, for making possible free rotatability between the sleeve and the supply hose, comprises two elements which are rotatable relative to each other. With one connecting member element the supply hose is connected releasably and non-rotatably and with the other connecting element the sleeve is connected also releasably and non-rotatably, in each particular instance with the aid of a cap nut adapted to be screwed onto the connecting member element concerned. The screwing-off and screwing-on of the cap nut necessary for separation and rejoining of the sleeve and connecting member represents in each particular instance an extremely inconvenient and time-consuming working step.

In the case of a similar, dental handpiece known from German Utility Model No. 72 06 582, the connecting member is designed in one piece, whereas for the releasable and freely rotatable connection between the sleeve and the connecting member on the outer side of the latter there is mounted, on a sleeve rotatable on the connecting member, a coupling hook which snaps under the influence of a spring rearwardly of an outer annular collar of the sleeve and is releasable by radial finger pressure in opposition to the spring effect.

Apart from the complicated design of this arrangement, the externally located coupling hook is disturbing and is, like the annular collar, subjected to soiling which through the agency of uneasy actuation can lead to blocking of the coupling hook designed as a two-armed lever. Additionally, actuation of the coupling hook also represents a separate working step during the separation of sleeve and connecting member.

The invention has been developed primarily, though not exclusively, with a view to provide a dental handpiece of the type mentioned at the outset, wherein both separation and also re-joining of the holding sleeve and the connecting member may take place simply and in time-saving manner.

According to the invention there is provided a dental handpiece comprising:
- a holding sleeve by which the handpiece may be manually manipulated;
- a tool-drive unit mounted at one end of the said sleeve and adapted for operation by a fluid pressure medium;
- a connecting member releasably connected to said sleeve at the opposite end thereof, said connecting member and said sleeve being relatively rotatable and said connecting member being adapted to be coupled releasably and non-rotatably with a fluid pressure supply hose;
- first fluid pressure lines provided in said holding sleeve and second fluid pressure lines provided in said connecting member, said first and second lines being in communication with each other and serving to convey fluid pressure media between said supply hose and said drive unit and/or associated consumers of fluid pressure media;
- a guide pin provided on said connecting member and a receiving passage provided in said holding sleeve in order axially to receive said guide pin and to connect together said holding sleeve and said connecting member, said second fluid pressure lines extending generally longitudinally through said guide pin and also extending transversely outwardly to respective outlet apertures axially spaced along the outer periphery of said guide pin;
- pairs of axially spaced seals arranged to seal said guide pin in said receiving passage, each pair of seals having a respective outlet aperture located therebetween;
- abutment means provided on said holding sleeve and on said connecting member and engageable, upon insertion of said guide pin in said receiving passage, in order to define a releasable, engaged position of said connecting member relative to said holding sleeve;
- and annular ducts provided in the wall of said receiving passage and registering one with each of said outlet apertures when said connecting member is in said engaged position, each duct communicating with a respective one of said first fluid pressure lines.

Thus, in a construction according to the invention, a separate working step e.g. the actuation of the cap nut or of the coupling hook in the known constructions, during separation or re-joining of the sleeve and the connecting member becomes superfluous, since for separation it is merely necessary to pull apart the holding sleeve and the connecting member with its guiding pin (whilst overcoming any clamping force tending to maintain the engaged position), in the sense of self-release, and on rejoining to push them one within the other, and this can be effected practically at great speed. Due to this high-speed coupling and in consequence of the fact that on adopting the engaged or snap-in position, i.e. on mutual engagement of the abutment means, the outlet apertures of the guiding pin are brought into communication with the annular ducts of the holding sleeve due to the arrangement of the sealing rings, without risk of leakage, the guarantee of entirely satisfactory media transfer or media passage is provided. Furthermore, the advantage is achieved that, subject to separation of the connecting member and the holding sleeve, the latter can be quite readily sterilised due to its sealing ring freedom. Also, the sleeve separated-off in the aforementioned rapid manner can, without it being necessary to pay attention to a pre-determined oiling aperture, be readily and rapidly attended-to or serviced, in that into the open guiding pin push-in end the nozzle or jet of an oil spray can is directed and then the spray-can dispensing valve is actuated, without any occurence of oil damming-up.

It is true that German Auslegeschrift No. 23 34 448 already discloses a dental handpiece wherein out of the periphery of the guiding pin between two packing rings an outlet aperture of a coolant line opens radially, the holding sleeve having at its inner wall also one annular duct associated with the said outlet aperture and from which extends the coolant line section leading to the consumption location. In the case of this known handpiece, however, the holding sleeve does not contain a pressure-air operated tool-driving unit, but a shaft driving the dental implement arranged at one end of the sleeve. The connecting member arranged at the other end of the sleeve is designed as a drive element having driving sockets emerging axially into a hollow-design guiding pin passing into engagement with the shaft of the holding sleeve on establishing the releasable and freely rotatable connection of the holding sleeve and the driving element. Since, in the case of this known handpiece, there is no pressure-air-operated driving unit, there is also no requirement for the arrangements of further medium lines, although in addition to the one coolant line, for example for cooling air, it would be expedient to have the second coolant line, for example for cooling water. To this must be added the fact that, in the known handpiece at the connecting member, there is again arranged a coupling hook snapping under the influence of a spring rearwardly of an inner annular collar of the sleeve and which due to a radially displaceably mounted pin can be brought into the snap-out position against the action of the spring. Thus, here again, actuation of the coupling hook involves, on separation of sleeve and connecting member, a special working step which is obviated in advantageous manner by the construction according to the invention.

In the handpiece according to the invention, the maintenance of the engaged position may be achieved solely by the resilience of the seals. However, additionally there may be provided, on the outer wall of the guiding pin an annular groove and in the wall of the receiving passage of the sleeve at least one detent ball mounted in a recess, which said ball, projecting under the influence of a spring with the smaller portion of a surface beyond the surface of the passage wall, engages into the annular groove and, against the action of the spring, during pulling apart of pushing one within the other of the sleeve and the connecting member, is adapted to be displaced out of the annular groove.

Especially advantageous media transfer results may be obtained if at least one of the outlet apertures is provided in an annular duct associated with it and arranged on the outer periphery of the guide pin.

Especially satisfactorily guided seating of the guiding pin in the sleeve may be achieved if the guiding pin extends over a large portion of the length of the sleeve, for example over a quarter up to a third of the length of the sleeve, into the latter. In this connection, in particular in the case of handpieces having a cranked portion or knee angled-over relative to the sleeve, it is expedient if the guiding pin extends over approximately half the length of the sleeve into the latter. Due to the well guided seat (achieved in each particular instance) of the guiding pin in the sleeve, the result is achieved that the dentist, during dental treatment, can rotate the grasping sleeve especially readily relative to the connecting member.

Advantageously, the guiding pin has a plurality of sections of varying diameter which, towards the free end of the guiding pin, are arranged to follow each other whilst becoming stepwise smaller. Thereby, also introduction of the guiding pin into the sleeve is facilitated. Again for achieving a satisfactorily guided seating of the guiding pin in the sleeve, the guiding pin may have a central section of greater length than the other sections, in which connection expediently the radially opening outlet apertures are arranged in guiding pin sections having a shorter length than the central section.

An expedient embodiment consists in that the connecting member is provided with at least one externally actuable control valve associated with a media passage duct, the control valve being optionally arranged in particular in a media passage duct conveying cooling water.

DESCRIPTION OF PREFERRED EMBODIMENTS

Figure 1:
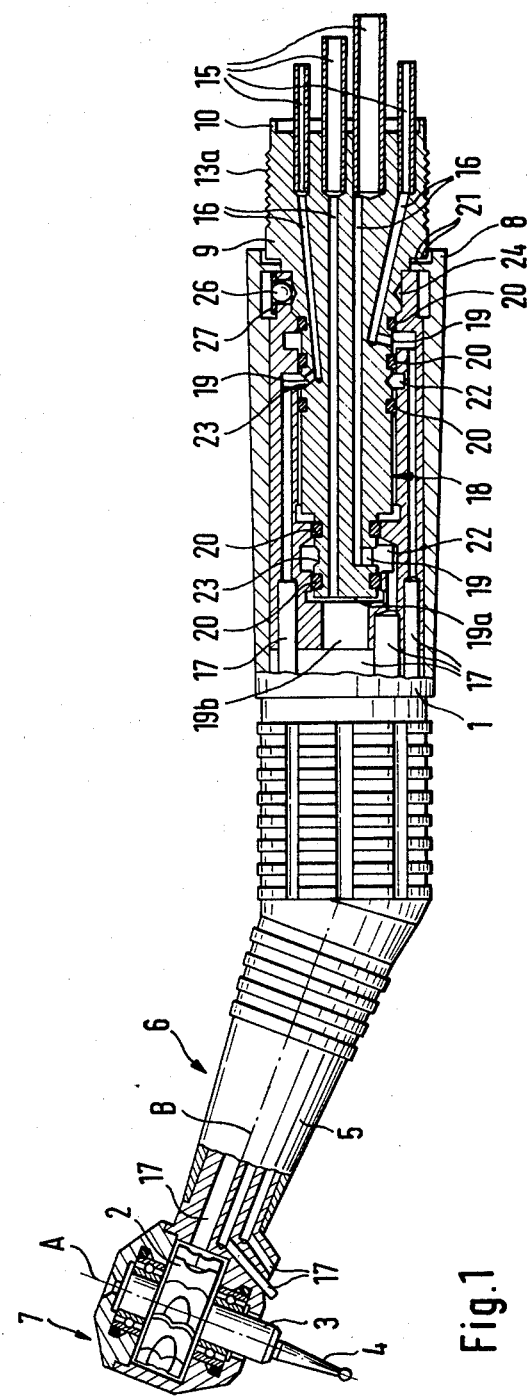
FIG. 1 is a longitudinal sectional view of a dental handpiece according to the invention.

The dental handpiece shown comprises a holding sleeve 1 having at one end a tool-drive unit 2 operated by compressed air. The drive unit 2 is designed in the form of an air turbine having a hollow rotor shaft 3 into which a tooth treatment implement 4 is inserted. Connected to the sleeve 1 is the shank 5 of a knee or cranked portion 6 bent-over at an oblique angle relative to the sleeve 1. Arranged at the end of the shaft 5 is a head 7 containing the drive unit 2, the axis 8 of the rotor shaft 3 extending approximately at right angles to the axis B of the shank 5.

Arranged at the end of the sleeve 1 remote from the knee 6, and releasable from the latter and freely rotatable relative thereto, is a cylindrical connecting member 9. At the end 10 of member 9 remote from the sleeve 1 there is connected releasably, but non-rotatably, a flexible supply hose (not shown) conveying pressure air and other fluid pressure media to or from the sleeve. For this purpose, the supply hose has at its connecting member end, in known manner, a hose end member 11 via which a hose retaining nozzle 12 connecting the hose with the hose end member is fixed. Finally, there is also disposed on the hose end member 11 an axially secured cap nut 13 adapted to be screwed onto an external screwthread 13a of the connecting member 9, whereby the hose end member 11 and the connecting member 9 can, with interpositioning of a sealing disc 14, be pulled firmly towards each other and connected to each other. Due to the equipment, (known per se) of the right-end 10 in the drawing of the connecting member 9 with inlet sockets 15 discussed hereinbelow, it is possible to connect the handpiece to conventional supply hose couplings.

Figure 2:
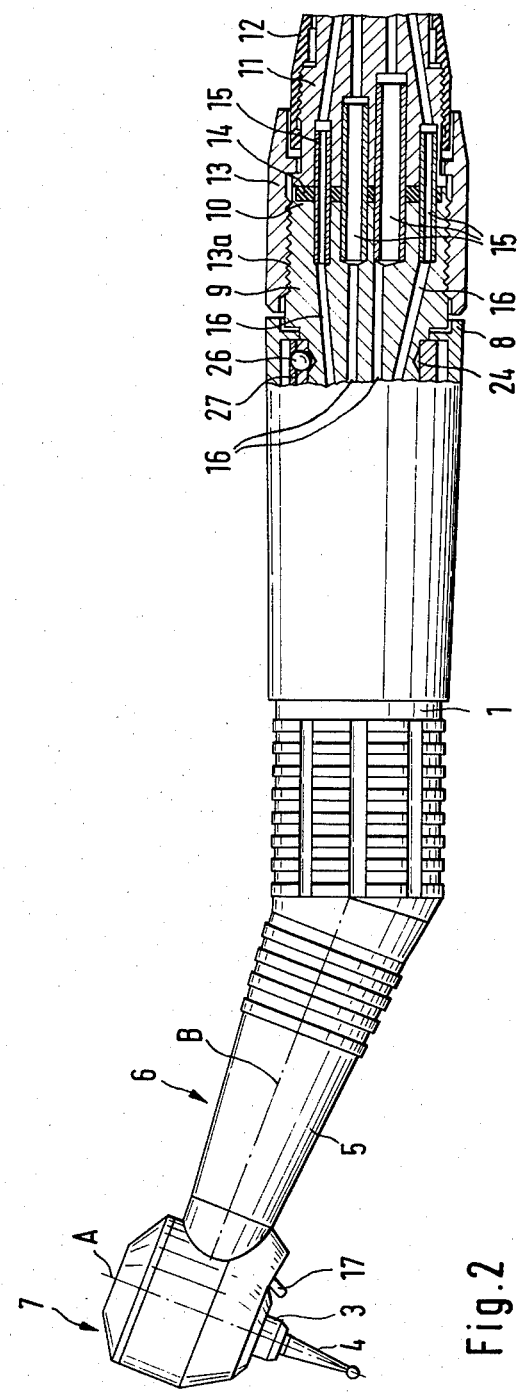
FIG. 2 shows the handpiece according to FIG. 1 connected to a fluid pressure media supply hose.

The connecting member 9 is provided with generally axially extending (second) fluid pressure supply lines in the form of ducts 16 having four inlet sockets 15 and which, when the sleeve 1 and the connecting member 9 are connected with each other, are connected to (first) fluid pressure supply lines in the form of lines 17 extending to fluid pressure media consumers of the handpiece. The sealing disc 14 shown in FIG. 2 has appropriate passages for passage of the four entry sockets 15. One of the media lines 17 may be for supplying pressure air to the driving unit 2, a second for supplying cooling water to the zone of the tooth-treatment implement 4, a third for supplying cooling air to the zone of the tooth-treatment implement 4, and a fourth media line 17 for discharging the exhaust air of the driving unit 2. The connecting member 9 is provided with a guiding pin 18 which in cross section is round and which is adapted to be inserted axially into a receiving passage in the sleeve 1 (from the right-hand side in the drawings).

Also into the guiding pin 18, there extend the ducts 16 each of which terminates in an outlet aperture 19 which opens radially out of the periphery of the guiding pin 18. The outlet apertures 19 are axially distributed along the length of the guiding pin 18, whilst leaving mutual spacing. With this arrangement, the outlet apertures 19 are each located between two seals, for example packing rings 20, passing into abutment at the inner wall of the passage of the sleeve 1. The packing rings 20 extend about the periphery of the guiding pin 18 and project only slightly out of this peripheral surface.

The connecting member 9 and the grasping sleeve 1 are provided with abutment means (21) which limit the push-in movement of the guiding pin 18 on adopting a snap-in or releasable detent position. Out of this snap-in position, the guiding pin 18 is automatically releasable in simple manner by the drawing apart of the grasping sleeve 1 and connecting member 9, without it being necessary to manually employ any kind of detent means. At the inner wall of its receiving passage, the sleeve 1 has annular ducts 22 associated with the outlet apertures 19 of the guiding pin 18. On adopting the snap-in position, the annular ducts 22 pass into connection with the outlet apertures 19 of the guiding pin 18. From the annular ducts 22 extend the media lines 17 extending to the fluid pressure media consumption locations of the handpiece.

Figure 3:
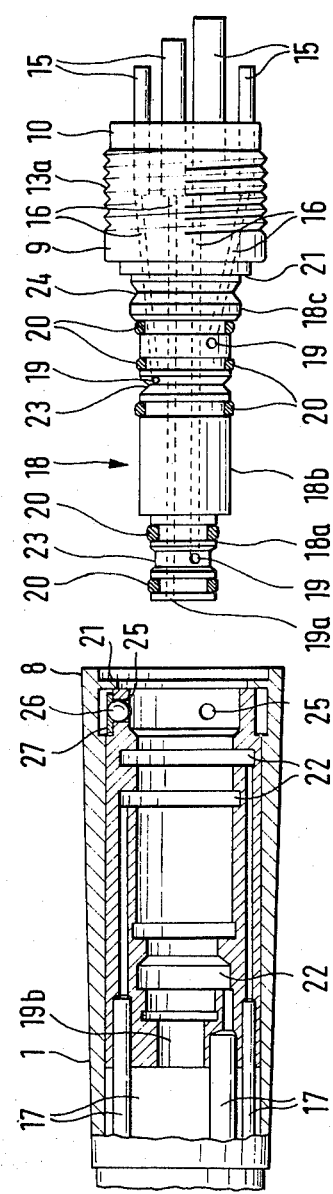
FIG. 3 is an exploded view of parts of the handpiece according to FIG. 1.

The two left-hand outlet apertures 19 (see FIGS. 1, 3 and 4) are provided in an annular duct 23 arranged on the outer periphery of the guiding pin 18, thereby achieving improved distribution of the medium during transfer out of the guiding pin 18 into the associated annular duct 22 of the sleeve 1.

One of the media passage ducts 16 of the guiding pin 18 has an outlet aperture 19a opening axially out of the free end of the guiding pin 18. This outlet aperture 19a passes into connection with an inlet aperture 19b of one of the four media lines 17 when the guiding pin 18 is pushed into the sleeve 1. This media line can serve for example for supplying the driving unit 2 with pressure air.

As will be apparent in particular from FIG. 1, the axial extent of the guiding pin 18 received in the passage of the sleeve 1 is equal to a substantial portion of the overall length of the sleeve.

The guiding pin 18 has a plurality of axial portions 18a, 18b, 18c of varying diameter and which, towards the free end of the guiding pin are arranged to follow each other in step-wise smaller arrangement. The central portion 18b of the guiding pin 18 is longer than the other portions 18a, 18c. It has been found to be expedient if the outlet apertures 19 are arranged in the portions of the guiding pin 18 of smaller length than the central section (18b).

The abutment means 21 are in each particular instance constituted by at least one annular shoulder arranged at the connecting member end of the guiding pin 18 and at the entrance 8 to the receiving passage of the sleeve 1. On inserting the sleeve 1 and the guiding pin 18 one within the other, the annular shoulders pass into mutual abutment whereby, as already stated hereinabove, adoption of a self-releasing detent position is determined.

If the clamping force for effecting the detent position by means of the resilience of the packing elements 20 alone is inadequate, there can be arranged for this purpose (as shown) on the outer periphery of the guiding pin 18 a separate annular groove 24 and in the wall of the receiving passage of the sleeve 1 at least one ball-type detent 26 housed in a recess 25. The detent 26 engages, with this arrangement, under the influence of a spring 27 and through the agency of a smaller portion of its surface, projecting beyond the inner face of the wall of the receiving passage, into the annular groove 24. For this purpose, the recess 25 has a base aligned with the inner face of the wall of the receiving passage, the said base being formed with an aperture which is smaller than the equatorial plane of the detent ball 26. During the push-in process or during the pulling-apart process, the detent ball is, against the action of the spring 27, displaced out of the groove 26, so that during the pulling apart process self-release of the detent position takes place.

The annular groove 26 is arranged at the connecting member end of the guiding pin 18 and the detent 26 is arranged at the entrance 8 of the sleeve 1.

Figure 4:
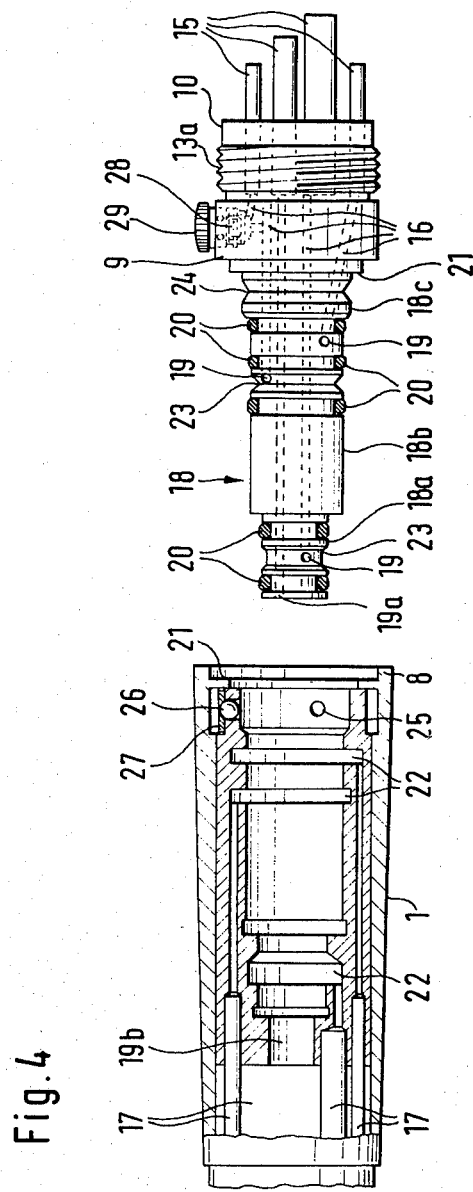
FIG. 4 shows a variant relative to FIG. 3.

In the case of the embodiment according to FIG. 4, the connecting member 9 is provided with at least one externally actuable control valve 28 associated with one of the ducts 16, for example the duct used for conveying cooling water. For actuation effective from the exterior, the control valve 28 has manipulating means 29 in the form of a rotatable knob.

I claim:
1. A dental handpiece comprising:
a holding sleeve by which the handpiece may be manually manipulated;
a tool-drive unit mounted at one end of the said sleeve and adapted for operation by a fluid pressure medium;
a connecting member releasably connected to said sleeve at the opposite end thereof, said connecting member and said sleeve being relatively rotatable and said connecting member being adapted to be coupled releasably and non-rotatably with a fluid pressure supply hose, said releasable engaged position of said connecting member and said holding sleeve is a detent position;
first fluid pressure lines provided in said holding sleeve and second fluid pressure lines provided in said connecting member, said first and second lines being in communication with each other and serving to convey fluid pressure media between said supply hose and said drive unit and/or associated consumers of fluid pressure media;

a guide pin provided on said connecting member and a receiving passage provided in said holding sleeve in order axially to receive said guide pin and to connect together said holding sleeve and said connecting member, said second fluid pressure lines extending generally longitudinally through said guide pin and also extending transversely outwardly to respective outlet apertures axially spaced along the outer periphery of said guide pin, and including an annular groove in the outer periphery of said guide pin and at least one ball-type detent housed in a recess in the wall of said receiving passage and spring-biased in a direction towards engagement in said annular groove;

pairs of axially spaced seals arranged to seal said guide pin in said receiving passage, each pair of seals having a respective outlet aperture located therebetween;

abutment means provided on said holding sleeve and on said connecting member and engageable, upon insertion of said guide pin in said receiving passage, in order to define a releasable, engaged position of said connecting member relative to said holding sleeve;

and annular ducts provided in the wall of said receiving passage and registering one with each of said outlet apertures when said connecting member is in said engaged position, each duct communicating with a respective one of said first fluid pressure lines.

2. A dental handpiece according to claim 1, wherein said annular groove is arranged adjacent to the connection of said guide pin to said connecting member and said ball-type detent is arranged adjacent to the entrance to said receiving passage.

3. A dental handpiece comprising:

a holding sleeve by which the handpiece may be manually manipulated;

a tool-drive unit mounted at one end of the said sleeve and adapted for operation by a fluid pressure medium;

a connecting member releasably connected to said sleeve at the opposite end thereof, said connecting member and said sleeve being relatively rotatable and said connecting member being adapted to be coupled releasably and non-rotatably with a fluid pressure supply hose;

at least one externally operable fluid flow control valve provided on said connecting member;

first fluid pressure lines provided in said holding sleeve and second fluid pressure lines provided in said connecting member, said first and second lines being in communication with each other and serving to convey fluid pressure media between said supply hose and said drive unit and/or associated consumers of fluid pressure media;

a guide pin provided on said connecting member and a receiving passage provided in said holding sleeve in order axially to receive said guide pin and to connect together said holding sleeve and said connecting member, said second fluid pressure lines extending generally longitudinally through said guide pin and also extending transversely outwardly to respective outlet apertures axially spaced along the outer periphery of said guide pin;

pairs of axially spaced seals arranged to seal said guide pin in said receiving passage, each pair of seals having a respective outlet aperture located therebetween;

abutment means provided on said holding sleeve and on said connecting member and engageable, upon insertion of said guide pin in said receiving passage, in order to define a releasable, engaged position of said connecting member relative to said holding sleeve;

and annular ducts provided in the wall of said receiving passage and registering one with each of said outlet apertures when said connecting member is in said engaged position, each duct communicating with a respective one of said first fluid pressure lines.

4. A dental handpiece according to claim 3, wherein said control valve is operable to control one of said second fluid pressure lines which conveys cooling water.

5. A dental handpiece according to either of claims 1 or 3, including an annular duct formed in the outer periphery of said guide pin, and at least one of said outlet apertures provided in said duct.

6. A dental handpiece according to either of claims 1 or 3, including a further one of said second fluid pressure lines extending generally longitudinally through said guide pin, said further pressure line terminating axially in an outlet aperture which is provided at the free end of said guide pin.

7. A dental handpiece according to either of claims 1 or 3, wherein the axial extent of said guide pin received in said passage is equal to a substantial portion of the length of said sleeve.

8. A dental handpiece according to claim 7, wherein the axial extent of said guide pin received in said passage is equal to a quarter up to one third of the length of said sleeve.

9. A dental handpiece according to claim 7, including a cranked portion connected to said holding sleeve, wherein the axial extent of said guide pin received in said passage is equal to approximately one half of the length of said holding sleeve.

10. A dental handpiece according to either of claims 1 or 3, wherein said guide pin has axial portions which are of successively smaller diameter towards the free end of said guide pin.

11. A dental handpiece according to claim 10, wherein a central axial portion of said guide pin has a greater axial extent than the axial extent of any other of said axial portions.

12. A dental handpiece according to claim 11, wherein said outlet apertures are provided in the periphery of said axial portions other than said central portion.

13. A dental handpiece according to either of claims 1 or 3, wherein said abutment means comprise an annular shoulder provided on said guide pin adjacent the connection of said guide pin to said connecting member and a further annular shoulder provided on said holding sleeve adjacent to the entrance to said receiving passage.

14. A dental handpiece according to either of claims 1 or 3, wherein said releasable engaged position of said connecting member and said holding sleeve is a detent position which is provided by the interengagement of said seals between the outer periphery of said guide pin and the periphery of said receiving passage.

* * * * *